(12) United States Patent
Wisniewski et al.

(10) Patent No.: US 7,194,924 B2
(45) Date of Patent: Mar. 27, 2007

(54) SYSTEM AND METHOD FOR BIOHAZARD DETECTION USING COMPRESSION

(75) Inventors: Michael A. Wisniewski, Owego, NY (US); Eugene Stradley, Owego, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 10/208,960

(22) Filed: Jul. 31, 2002

(65) Prior Publication Data

US 2004/0020266 A1 Feb. 5, 2004

(51) Int. Cl.
*G01N 1/22* (2006.01)
(52) U.S. Cl. .................... 73/863.21; 73/863.22
(58) Field of Classification Search ............ 73/863.21, 73/863.22, 864.33; 232/17, 19, 21, 30, 31, 232/32, 47, 53
See application file for complete search history.

(56) References Cited

U.S. PATENT DOCUMENTS

| | | | |
|---|---|---|---|
| 3,519,198 A | 7/1970 | Benoliel | |
| 3,647,203 A | 3/1972 | De Hart | 271/30 A |
| 4,175,140 A | 11/1979 | Bachmann et al. | 426/399 |
| 4,360,108 A | 11/1982 | Logothetis | 209/598 |
| 4,593,816 A | 6/1986 | Langenbeck | 206/425 |
| 4,718,809 A * | 1/1988 | Krasuski et al. | 414/797.7 |
| 4,786,295 A | 11/1988 | Newman et al. | 55/213 |
| 4,877,964 A | 10/1989 | Tanaka et al. | 250/455.1 |
| 4,987,767 A | 1/1991 | Corrigan et al. | 73/23.36 |
| 5,009,869 A | 4/1991 | Weinberg et al. | 423/210 |
| 5,109,691 A | 5/1992 | Corrigan et al. | 73/23.36 |
| 5,179,581 A | 1/1993 | Annis | 378/57 |
| 5,213,759 A | 5/1993 | Castberg et al. | 422/24 |
| 5,225,167 A | 7/1993 | Wetzel | 422/121 |
| 5,254,861 A | 10/1993 | Carpenter et al. | 250/573 |
| 5,322,603 A | 6/1994 | Kameda et al. | 204/158.2 |
| 5,325,795 A | 7/1994 | Nelson et al. | 110/236 |
| 5,328,847 A | 7/1994 | Case et al. | 435/291 |

(Continued)

FOREIGN PATENT DOCUMENTS

JP 7237153 A2 9/1995
WO WO91/09307 6/1991

OTHER PUBLICATIONS

*U.S. Postal Service Emergency Preparedness Plan for Protecting Postal Employees and Postal Customers from Exposure to Biohazardous Material and for Ensuring Mail Security Against Bioterror Attacks; Mar. 6, 2002; published by USPS.

(Continued)

*Primary Examiner*—Hezron Williams
*Assistant Examiner*—Ryan Christensen
(74) *Attorney, Agent, or Firm*—Burns & Levinson LLP; Jacob N. Erlich; Harvey Kaye

(57) ABSTRACT

The present invention includes a system and method for detecting contaminated objects, for example mail pieces, through use of a pinching device that compresses the objects, thereby possibly releasing potential contaminant-containing particles into the air in a closed chamber. Whatever particles are in the closed chamber mix with the air in the closed chamber and form cavity air, which is captured by a detection and alert mechanism.

18 Claims, 6 Drawing Sheets

U.S. PATENT DOCUMENTS

| | | | |
|---|---|---|---|
| 5,330,722 A | 7/1994 | Pick et al. | 422/121 |
| 5,345,809 A | 9/1994 | Corrigan et al. | 73/23.2 |
| 5,413,915 A | 5/1995 | Case et al. | 435/25 |
| 5,465,607 A | 11/1995 | Corrigan et al. | 73/23.36 |
| 5,480,032 A | 1/1996 | Pippin et al. | 209/583 |
| 5,493,363 A * | 2/1996 | Morita | 355/99 |
| 5,505,904 A | 4/1996 | Haidinger et al. | 422/24 |
| 5,585,575 A | 12/1996 | Corrigan et al. | 73/863.71 |
| 5,681,752 A | 10/1997 | Prather | 436/173 |
| 5,700,426 A | 12/1997 | Schmitthaeusler et al. | 422/29 |
| 5,786,598 A | 7/1998 | Clark et al. | 250/455.11 |
| 5,809,185 A | 9/1998 | Mitchell | 385/12 |
| 5,833,740 A | 11/1998 | Brais | 96/16 |
| 5,841,038 A | 11/1998 | Volz | 73/863.85 |
| 5,858,430 A | 1/1999 | Endico | 426/241 |
| 5,859,362 A | 1/1999 | Neudorfl et al. | 73/23.2 |
| 5,874,046 A | 2/1999 | Megerle | 422/68.1 |
| 5,876,960 A | 3/1999 | Rosen | 435/39 |
| 5,895,191 A | 4/1999 | Bonora et al. | 414/217 |
| 5,895,922 A | 4/1999 | Ho | 250/491.2 |
| 6,037,598 A | 3/2000 | Cicha | 250/455.11 |
| 6,051,189 A | 4/2000 | Wick et al. | 422/82.01 |
| 6,054,324 A | 4/2000 | Sullivan et al. | 436/174 |
| 6,062,977 A | 5/2000 | Hague | 454/341 |
| 6,087,183 A | 7/2000 | Zaromb | 436/178 |
| 6,132,784 A | 10/2000 | Brandt et al. | 426/258 |
| 6,183,691 B1 | 2/2001 | Swank et al. | 422/24 |
| 6,199,604 B1 | 3/2001 | Miyajima | 141/98 |
| 6,233,748 B1 | 5/2001 | Gieger et al. | 2/410 |
| 6,309,551 B1 * | 10/2001 | Suchecki et al. | 210/744 |
| 6,324,927 B1 * | 12/2001 | Ornath et al. | 73/864.33 |
| 6,427,524 B1 * | 8/2002 | Raspante et al. | 73/45.4 |
| 6,536,136 B2 * | 3/2003 | Saga | 34/417 |
| 6,737,029 B2 * | 5/2004 | Miller et al. | 422/300 |
| 6,742,703 B2 | 6/2004 | Esakov et al. | |
| 6,941,794 B2 * | 9/2005 | Strohmeyer et al. | 73/28.01 |
| 2002/0124664 A1 * | 9/2002 | Call et al. | 73/863.22 |
| 2002/0126008 A1 | 9/2002 | Lopez et al. | 340/540 |
| 2003/0110946 A1 * | 6/2003 | Lehman | 95/273 |
| 2003/0113922 A1 * | 6/2003 | Cordery et al. | 436/1 |
| 2003/0119175 A1 * | 6/2003 | Stradley et al. | 435/287.1 |
| 2003/0136203 A1 * | 7/2003 | Yoon | 73/864.33 |
| 2003/0138344 A1 * | 7/2003 | Mielnik et al. | 422/2 |
| 2003/0145664 A1 * | 8/2003 | Schwarz et al. | 73/863.22 |
| 2003/0222132 A1 | 12/2003 | Esakov et al. | |
| 2003/0233891 A1 * | 12/2003 | Cordery et al. | 73/863.21 |
| 2004/0020264 A1 * | 2/2004 | Megerle | 73/19.01 |
| 2004/0026491 A1 * | 2/2004 | Beckert et al. | 232/17 |
| 2004/0028561 A1 * | 2/2004 | Daugherty et al. | 422/99 |
| 2004/0255701 A1 * | 12/2004 | Strohmeyer et al. | 73/864 |

OTHER PUBLICATIONS

Copending U.S. Appl. No. 10/307,531, filed Nov. 27, 2002. Applicant: Eugene Stradley. Title: Apparatus For Testing For Particulate Contaminants In Depositories For Mail-Like Articles.

Copending U.S. Appl. No. 10/279,312, filed Oct. 24, 2002. Applicant: Clifford A. Megerle. Title: System and Method For Detecting Bio-Hazardous Particulates In Mail Handling Systems.

* cited by examiner

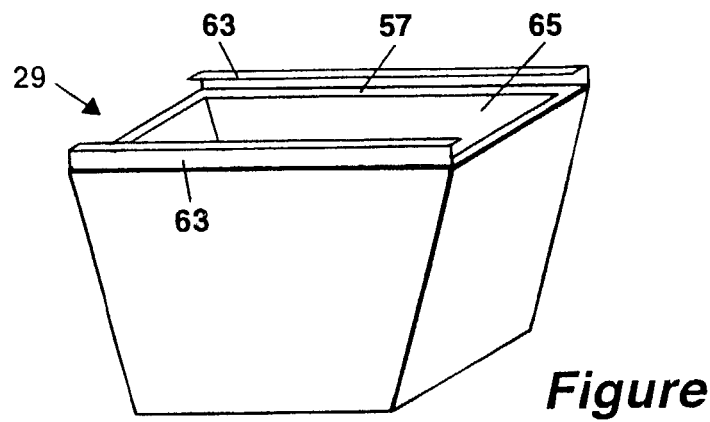
*Figure 3A*
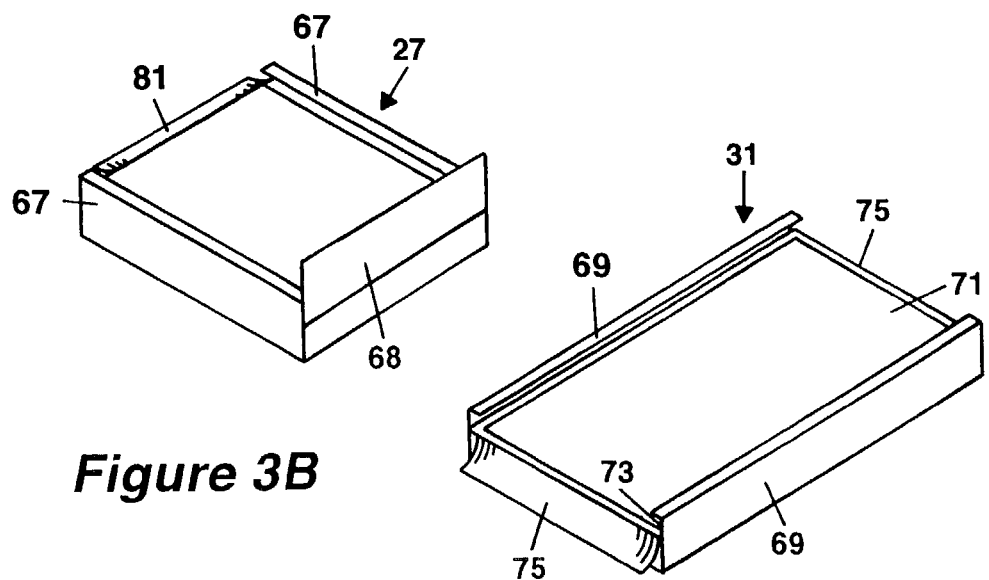
*Figure 3B*
*Figure 3C*

SYSTEM AND METHOD FOR BIOHAZARD DETECTION USING COMPRESSION

BACKGROUND OF THE INVENTION

This invention relates generally to the detection of hazardous material deposited in flat objects and, more particularly to the detection of biological hazardous material deposited in flat mail objects or the like and the isolation of such objects for decontamination or disposal.

The recent incidents of anthrax-laced letters being transported through the United States Postal Service (USPS) facilities to unsuspecting recipients has alarmed the nation and the world. Currently, the tainted letters are discovered after the recipient accepts delivery or by alert postal employees noticing white powder that could be anthrax on mail parcels sorting and distribution equipment, or themselves. There appear to be no current security devices or procedures that are available to intercept such letters at the earliest source of introduction into the USPS system, for example at the postal sorting facility.

Operating and maintaining high-speed mail handling machines is a major source of common variety dust in mail handling facilities. Experts believe that automatic mail processing systems may accidentally act as aerosolizing mechanisms. In the context of anthrax-bearing mail, mail processing devices which utilize pinch rollers or that involve high impact sorting or routing of processed mail may act to force spores from envelopes into the air. The "blow-down" of these machines in cleaning or maintenance operations also may cause anthrax spores to become aerosolized.

Currently, flat objects or letters are batch processed at a postal sorting facility for routing to a final destination. Mail tubs taken from mail collection boxes are emptied into a sorting bin containing objects from other mail collection boxes. The identity of the mail collection box where each object was deposited is lost when the mail tub is emptied into a sorting bin. Further, one single contaminated object can contaminate objects from several mail collection boxes. What is needed is a system that protects objects of mail, USPS employees employee workspaces and ultimately mail recipients from contamination while tracing the source of the contamination.

SUMMARY OF THE INVENTION

The present invention includes a system and method for detecting contaminated objects through use of compression. The system includes a pinching subsystem that compresses incoming objects thereby possibly forcing particles to be released into the air within a cavity formed by a closed chamber that is operably connected to the pinching subsystem. Whatever particles are released can mix with the air in the cavity forming what is herein referred to as "cavity air", and the cavity air is captured by a cavity air processing subsystem which is operably connected to the closed chamber. The system further includes a sealable inlet through which objects are deposited into the cavity and a hooded and sealed hamper that is operably connected to the pinching subsystem to receive objects after they have passed through the pinching subsystem.

The pinching subsystem of the present invention can include any type of pinching or squeezing device, for example, a pair of juxtapositional rollers and a pinching subsystem power supply, which may be a motor, to rotate the pair of juxtapositional rollers. The juxtapositional rollers can be a left roller and a right roller, in which the left roller is substantially adjacent to the right roller, and there is optimal spacing between the left and right rollers to allow constricted passage of the objects between the rollers. The left roller and right roller rotate in opposite directions. Other roller configurations may also be acceptable within further embodiments of this invention such as for example, a top and bottom roller.

The cavity air processing subsystem receives the cavity air, subjects the cavity air to at least one test for contamination, and sets an indication of the results obtained from the test(s). A decision can be made with respect to further handling of the object(s) based on the indication. The cavity air processing subsystem can optionally include a pathogen detection subsystem that tests the cavity air for contamination and sets the indication whenever the cavity air is contaminated. A tube can optionally be inserted into the cavity to draw the cavity air from the cavity.

The system may optionally include a controller capable of sequencing operations of the various components of the system including but not limited to the pinching subsystem and the cavity air processing subsystem. The controller may receive a first signal from the pathogen detection subsystem whenever the cavity air is contaminated. The first signal may optionally cause the controller to transmit the indication through a computer network connection to network receptors such as other nodes on the network. The controller may also optionally transmit a second signal to the pinching subsystem power supply to stop the pinching subsystem if the pathogen detection subsystem detects a contaminant in the cavity air.

The sealable inlet of the present invention provides an opening to the closed chamber through which objects may be deposited. The sealable inlet defines a sealable inlet edge that is spanned, during operation, by a cover, for example, a slidable shutter. A first substantially airtight seal is formed between the shutter and the sealable inlet edge. When the sealable inlet is covered, there is no gas exchange between the environmental air and the cavity air within the closed chamber.

The sealable inlet can also optionally accommodate an interlocking device, for example a tub, for transporting objects from another location, for example a mailbox, to the closed chamber. The tub defines an interior and has a tub rim. The tub rim is compatibly shaped with the sealable inlet edge forming a second substantially airtight seal. The tub can further include a sealable slidable tub lid covering the tub rim, forming a third substantially airtight seal. The three airtight seals substantially isolate the contents of the cavity and the contents of the tub from gas exchange with the ambient workspace and outside environment. In operation, when the objects are to be emptied from the tub to the cavity, the tub is placed inverted upon the closed chamber near the shutter. The tub is then slid against the shutter, thereby opening the shutter while at the same time sliding aside the tub's slidable lid, thereby opening the tub. After the tub lid is slid aside, the objects in the tub can fall into the cavity. After the tub is emptied, the tub is slid towards the tub lid. The shutter moves back over the sealable inlet as the tub is slid over the tub lid. When the tub is completely covered by its lid, the closed chamber will be completed covered by the shutter. During this process exchange of air between the ambient workspace and the tub/cavity is prevented by air barrier seals around the slidable tub lid and the shutter.

The system can optionally include a transport device such as a conveyor belt within the cavity. If present, the transport device can be driven by a transport power supply such as a motor. The transport device forms a path and direction of normal travel from the sealable inlet to the pinching subsystem, and conveys objects along the path and direction of normal travel. The controller may transmit a third signal to the transport power supply stopping the transport device if the pathogen detection subsystem detects a contaminant.

The system can also optionally include a separator mechanism for preparing the objects for entry into the pinching subsystem, primarily for separating them from each other so that they can fit properly in the intentionally-narrow opening of the pinching subsystem.

The method of the present invention for detecting contaminated objects includes the steps of accepting at least one object into a sealable inlet of a cavity, and directing the object(s) in a predetermined direction. The method further includes the steps of squeezing the object(s) by a pinching subsystem to release particles associated with the object(s) into the air in the cavity forming cavity air. The step of squeezing can optionally include the steps of moving the object(s) between two rollers and rotating the rollers while the object(s) moves between the rollers so that the object(s) is simultaneously moved through the rollers and pinched. The method further includes the steps testing the cavity air for contamination, and providing an indication if the contents are contaminated. The method of the present invention can optionally include the steps of initiating contamination processing if the cavity air is contaminated, or resetting the indication and continuing to receive objects if cavity air is not contaminated.

The method of the present invention can optionally include the steps of placing the object(s) into a tub having a tub rim, inverting the tub on top of the cavity, matably connecting the tub rim with a sealable inlet edge of the cavity, and depositing the object(s) into the cavity from the tub. The method can further optionally include the step of preparing the object(s) for entry into the pinching subsystem. The method can further optionally include the step of sequencing the directing, squeezing, and testing steps. The method can further optionally include the step of transmitting the indication through a computer network.

For a better understanding of the present invention, together with other and further objects thereof, reference is made to the accompanying drawings and detailed description. The scope of the present invention is pointed out in the appended claims.

BRIEF DESCRIPTION OF THE SEVERAL VIEWS OF THE DRAWING

FIG. 3A is a pictorial view of a tub of the illustrative embodiment of the present invention;

FIG. 3B is a pictorial view of a shutter that is matably and slidably positioned atop the sealable inlet of the illustrative embodiment of the present invention;

FIG. 3C is a pictorial view of the tub lid that is matably and slidably positioned atop the tub of the present invention;

DETAILED DESCRIPTION OF THE INVENTION

The present invention is now described more fully hereinafter with reference to the accompanying drawings in which the illustrative embodiment of the present invention is shown.

Figure 1:
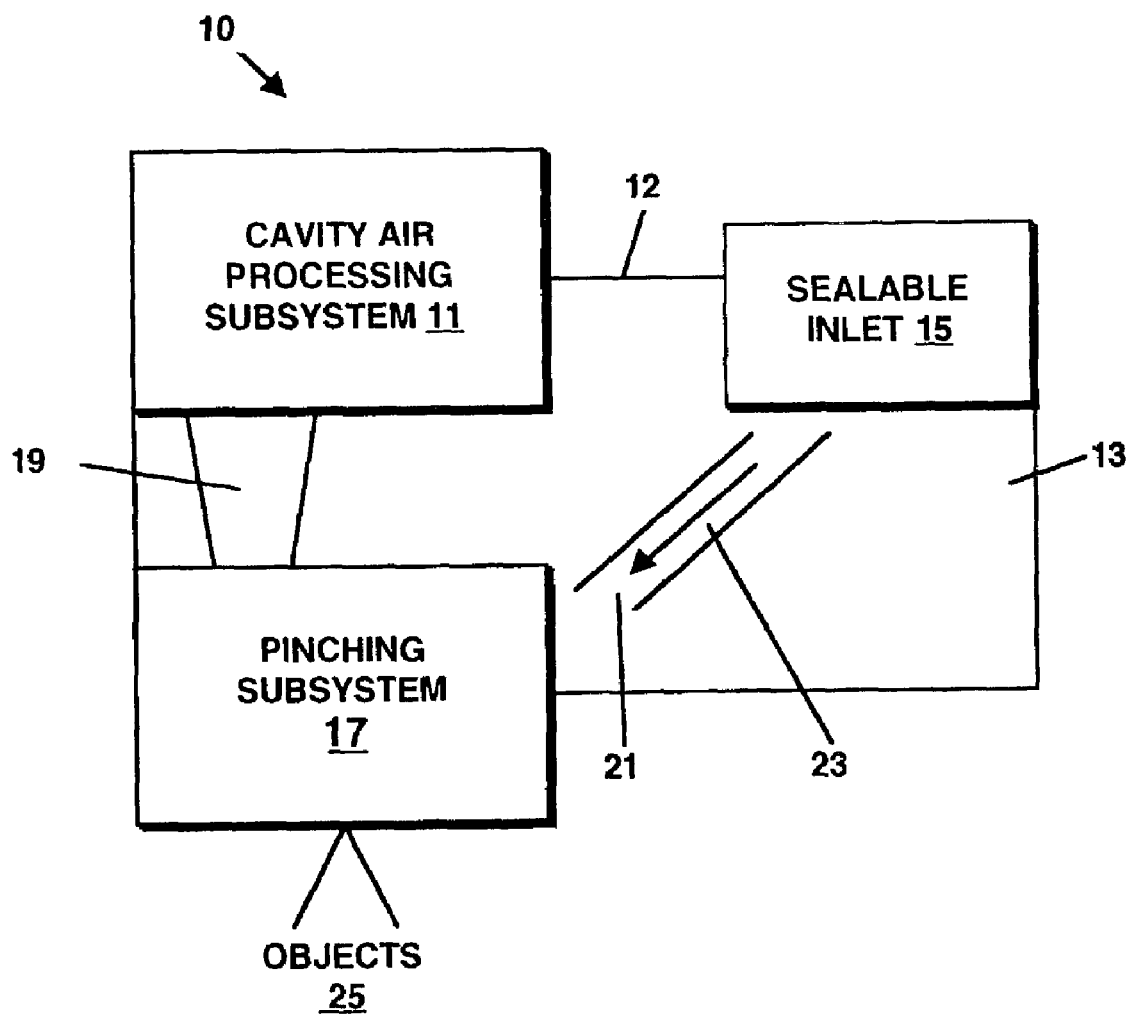
FIG. 1 is a schematic block diagram of the system of the present invention.

Referring now to FIG. 1, the system 10 of the present invention includes a closed chamber 12 forming a closed chamber cavity 13, wherein the chamber 12 has a sealable inlet 15 through which objects enter the cavity 13. The entering objects travel path 21 in direction of travel 23 and enter a pinching or squeezing subsystem 17 which performs a compression on the entering objects. The compressed objects may emit particles that mix with the air in the cavity to form cavity air 19 that enters the cavity 13 and are drawn into cavity air processing subsystem 11. Objects 25 exit the cavity 13 through pinching subsystem 17. The cavity air processing subsystem 11 captures the cavity air 19 and tests it for contamination.

Figure 2:
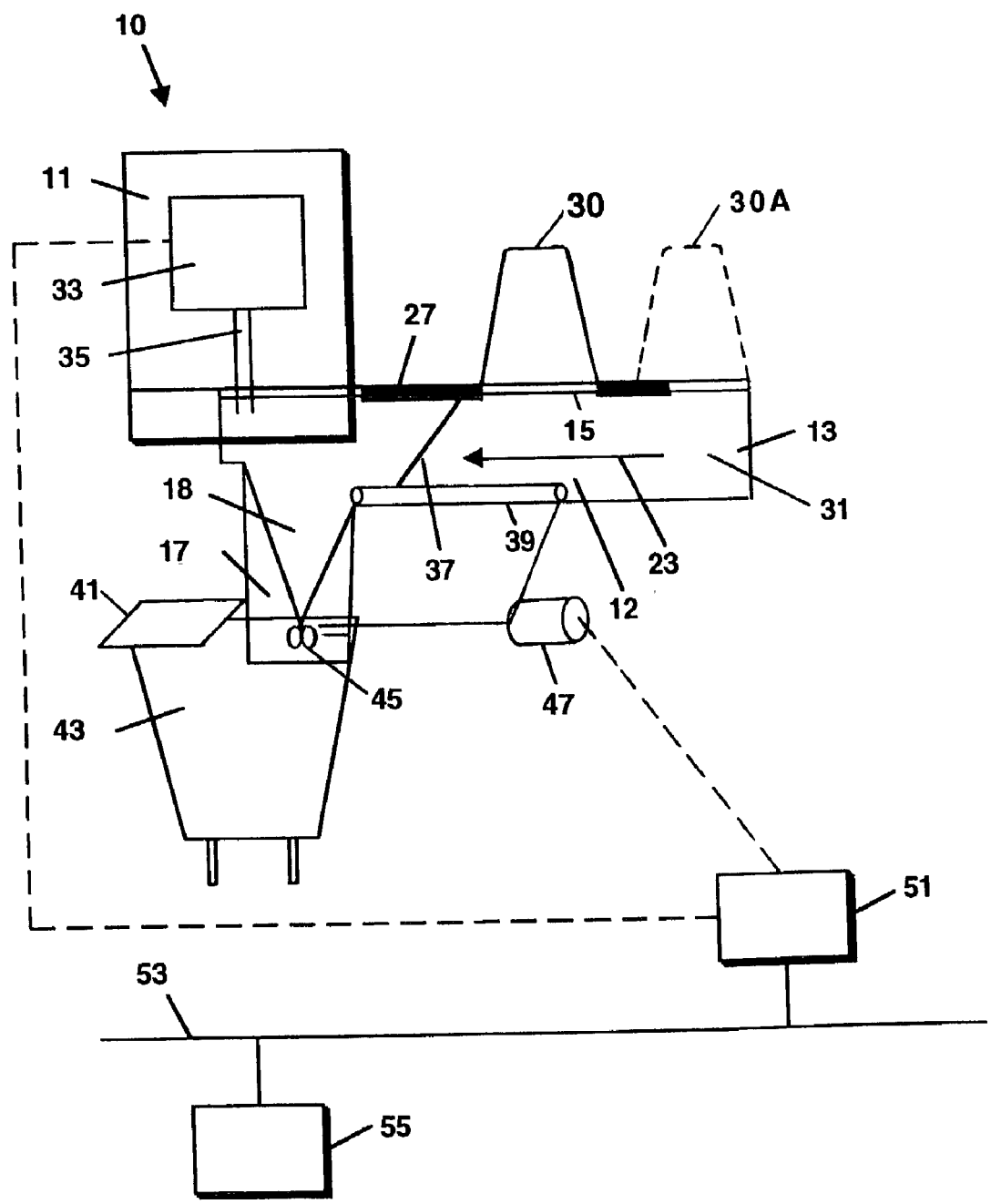
FIG. 2 is a pictorial view of the illustrative embodiment of the system of the present invention showing an inverted tub being unloaded and a phantom view of the inverted tub showing the inverted tub in pre-unloading position.

Referring now to FIG. 2, the illustrative embodiment of the present invention includes system components cavity air processing subsystem 11, chamber 12 forming cavity 13, sealable inlet 15, and pinching subsystem 17 embodied in an operational system 10 in which the objects 25 are, for example, mail pieces. In system 10, shutter 27 slides aside and inverted tub 30, shown in pre-unloading (dotted line 30A) and unloading (solid line 30) positions is slid into position atop sealable inlet 15. The mail pieces in inverted tub 30 fall onto a transport means such as conventional conveyor belt 39 or conventional rollers (not shown) driven by power supply 47. The mail pieces can be prepared for entry into the pinching subsystem 17 by a separator mechanism 37 such as conventional paddles or herringbone rollers that separate mail pieces into single pieces or small clusters of mail. In the illustrative embodiment of the present invention, the mail pieces then enter the pinching subsystem 17 that illustratively includes a chute 18 and a set of pinch rollers 45. The pinch rollers 45 compress the mail pieces as they pass into hamper 43 which is fitted with sealable hood 41 to maintain isolation between system 10 and the outside environment. The compression of the pinch rollers 45 can release particles and the particles can mix with air in the cavity to create cavity air 19 (as shown in FIG. 1) that remains in cavity 13 while the mail pieces drop into hamper 43.

Continuing to refer to FIG. 2, cavity air processing subsystem 11 captures cavity air 19 through tube 35, which provides a conduit from cavity 13 into the pathogen detection subsystem 33 which can contain a conventional contaminant sensor such as BIONI or Biological Aerosol Real Time Sensors manufactured by Pacific Scientific Instruments and the Biological Aerosol Warning Systems I, PCR system developed by the assignee of this application, or any real-time sensor for airborne contaminants. When contaminated cavity air is detected, cavity air processing subsystem 11 notifies controller 51, and controller 51 sets an indication.

Continuing to refer to FIG. 2, controller 51 can be a personal computer, a programmable logic controller, or an embedded controller, among other possibilities. Controller 51 can send commands to and receive data and status from cavity air processing subsystem 11. Controller 51 can also control conveyor belt 39 and pinching subsystem 17 by controlling power supply 47. Controller 51 can also interface with network connection 53, which is shown in FIG. 2 as a local area network but which can be any wired or wireless network in which electronic communications are enabled. For example, information about the origin of the contents of inverted tub 30 can be fed into controller 51 which can contain an emergency alert notification system or any other conventional or custom program. Thus when a contaminant is detected and an indication is set, the operator and network receptors 55 listening for such indications are provided information associated with the contamination that could assist in tracking the source of the contamination. Controller 51 can also control the movement of inverted tub 30 (perhaps through a conventional actuation mechanism, not shown) so that inverted tub 30 can be remotely and automatically moved into the correct position to unload objects.

Figure 4A:
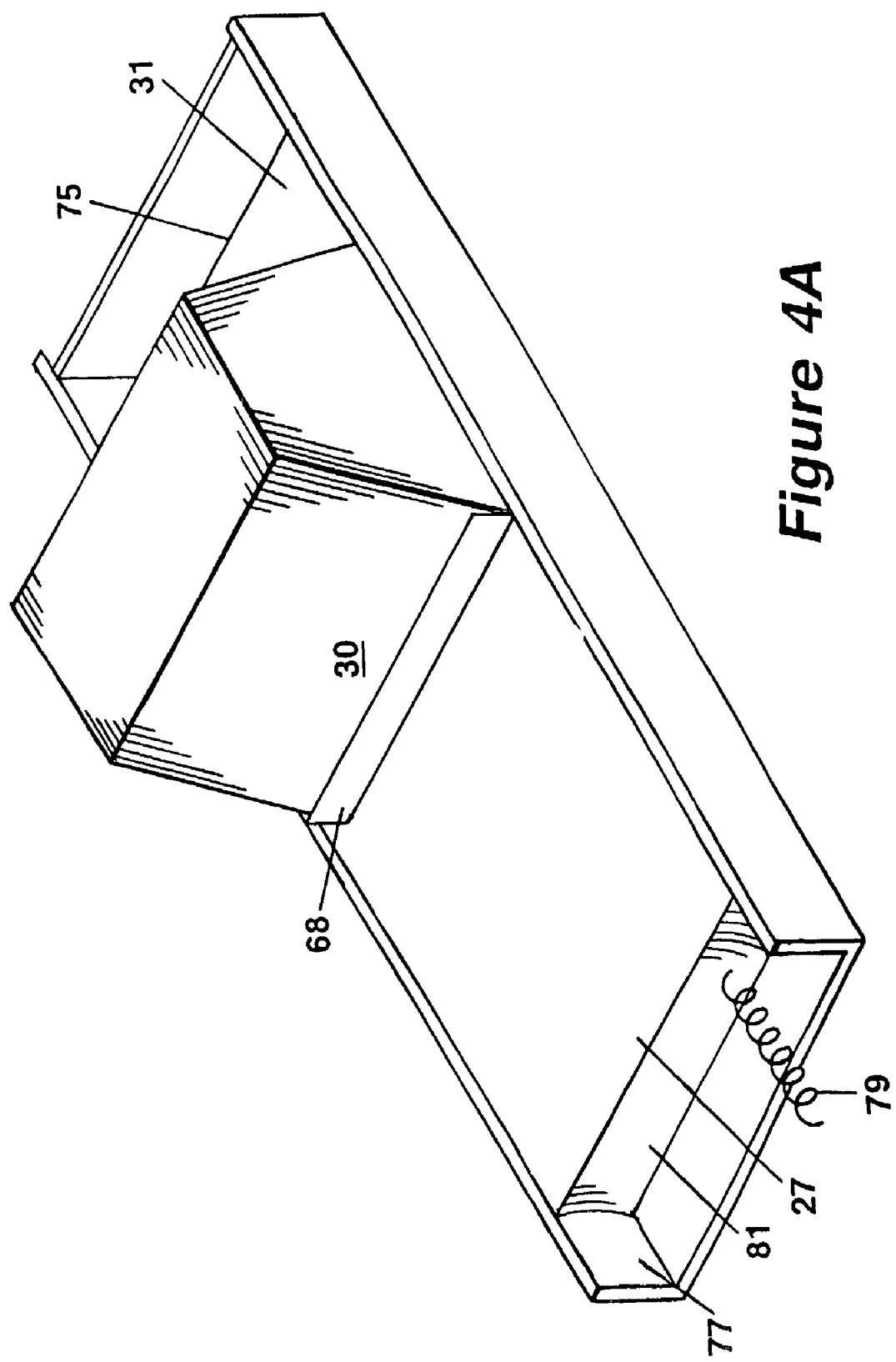
FIG. 4A is a pictorial view of the inverted tub of the illustrative embodiment of the present invention where the inverted tub is in unloading position with the shutter and tub lid slid away from the sealable inlet.
Figure 4B:
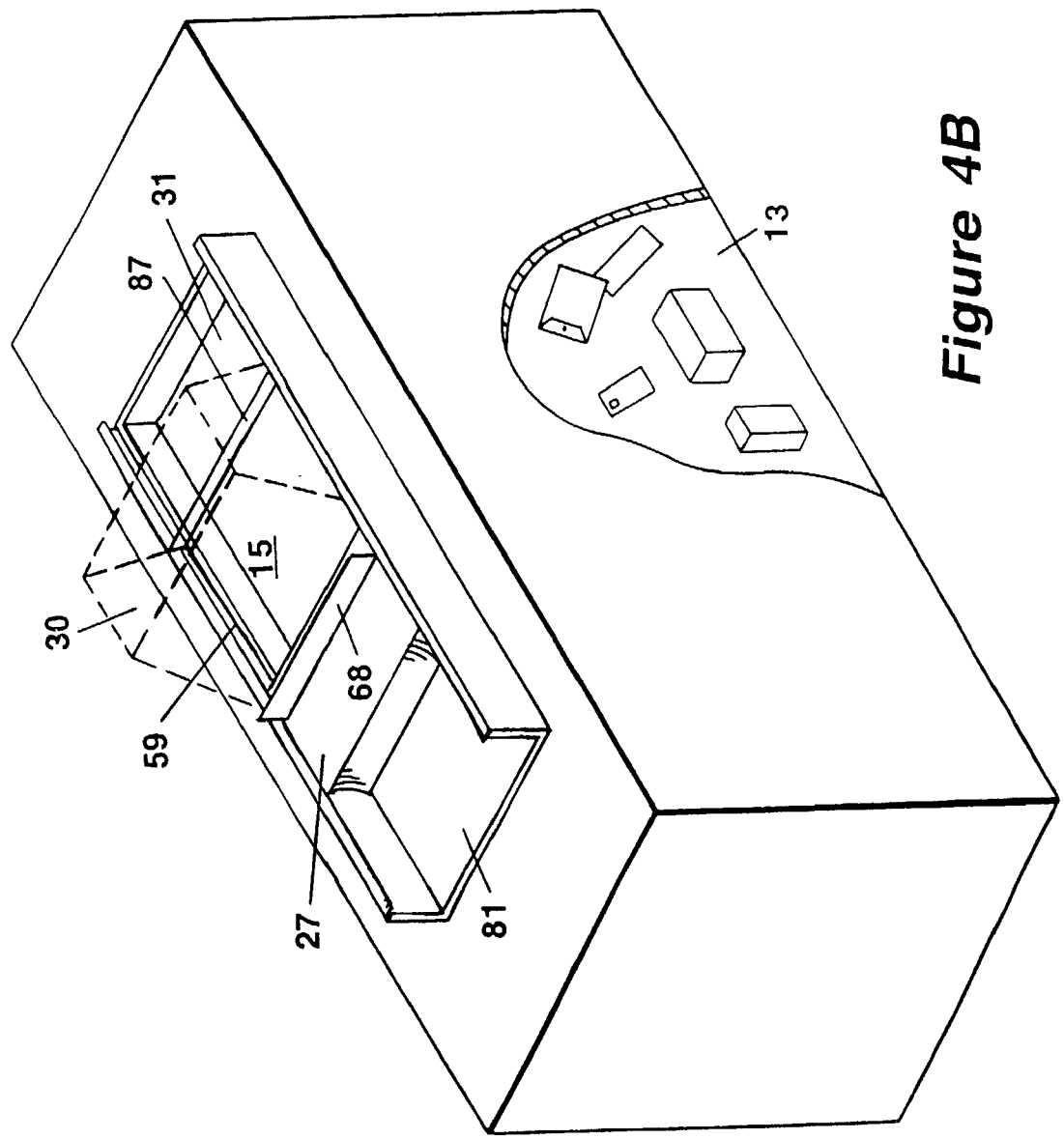
FIG. 4B is a transparent pictorial view of the inverted tub and a segment of the chamber into which objects are deposited from the inverted tub, in which the inverted tub is in unloading position showing the lid stopper of the slidable tub lid and shutter push of the slidable shutter.

Referring primarily to FIG. 3A, tub 29 of the illustrative embodiment of the present invention is shown without tub lid 31 (FIG. 3C). Tub rim 57 is shown herein with four sides but can be any shape. In the illustrative embodiment, two sides of tub rim 57 are fitted with rim lid interfaces 63 that are herein L-shaped but can be any shape. Rim lid interfaces 63 are slidably held within both lid runner 73 (FIG. 3C) and chamber opening runner 77 (FIG. 4A). Rim lid interfaces 63 allow inverted tub 30 to be slid into unloading position atop sealable inlet 15 (FIG. 4B). Tub interior 65 holds objects that will be emptied through sealable inlet 15 into cavity 13 (FIG. 4B) when inverted tub 30 is in unloading position (FIGS. 4A,B).

Referring primarily to FIG. 3B, shows shutter 27 including shutter runners 67 along two edges of shutter 27. The shutter 27 of the illustrative embodiment is preferably slidable, but can be hinged or removable in any other way. Shutter runners 67 slidably fit within chamber opening runners 77 (FIG. 4A) allowing the shutter 27 to slide away from sealable inlet 15 (FIG. 4B) as inverted tub 30 is slid into unloading position.

Referring primarily to FIG. 3C, lid underside 71 of tub lid 31 is shown with lid runners 73 into which rim lid interfaces 63 (FIG. 3A) slide to cover tub 29 (FIG. 3A). Lid chamber runners 69 slidably mate with chamber opening runners 77 (FIG. 4A). On edges where there are no lid runners tub lid 31 is sealed against gas exchange with full coverage lid tub seals 75.

Referring primarily to FIGS. 4A–B, the illustrative embodiment of the present invention can optionally include a specialized sealed inverted tub 30 that, when atop sealable inlet 15 having sealable inlet edge 59, can become unsealed with respect to cavity 13 but not with respect to the environment. The inverted tub 30 can be constructed of any rigid or semi-rigid material and can be any shape. The inverted tub 30 holds mail until it is inverted and slid or placed (perhaps automatically) over the sealable inlet 15 as described in detail below. A shutter 27, preferably slidable, retractable, sealable, and constructed of any rigid or semi-rigid material, seals the cavity 13 from the outside environment and covers the sealable inlet 15 until inverted tub 30 is inverted and moved into an unloading position. Inverted tub 30 can be positioned adjacent to the shutter 27 such that a section of the tub rim 57 (FIG. 3A) is in contact with shutter push 68. As inverted tub 30 is moved toward shutter 27 against shutter push 68, shutter 27 simultaneously slides away from sealable inlet 15, thus opening sealable inlet 15 so that mail pieces from inverted tub 30 can drop into cavity 13. While inverted tub 30 is being slid into unloading position, tub lid 31 is being held in position by lid stopper 87. After the mail is unloaded, inverted tub 30 is slid over tub lid 31 while simultaneously shutter 27 slides back into a closed position over sealable inlet 15, perhaps through the biasing of shutter spring 79. Before, during, and after loading and unloading, seals against ambient air exchanged are maintained through by lid tub seal 75 and shutter seal 81.

In an alternative embodiment (not shown), the shutter 27 can remain sealed over sealable inlet 15 until the inverted tub 30 is in place over the sealable inlet 15. In this embodiment, the shutter 27 is positioned below the tub lid 31 until the inverted tub 30 is correctly positioned above the sealable inlet 15 and locked into position creating a seal. Then the shutter 27 is moved into position to open sealable inlet 15, tub lid 31 is moved into position to open inverted tub 30, and the mail can drop from the inverted tub 30 into cavity 13. After the inverted tub 30 is emptied, the shutter 27 is moved under the inverted tub 30 to close sealable inlet 15. When inverted tub 30 is to be removed, lid 31 is moved into position to close inverted tub 30.

Figure 5:
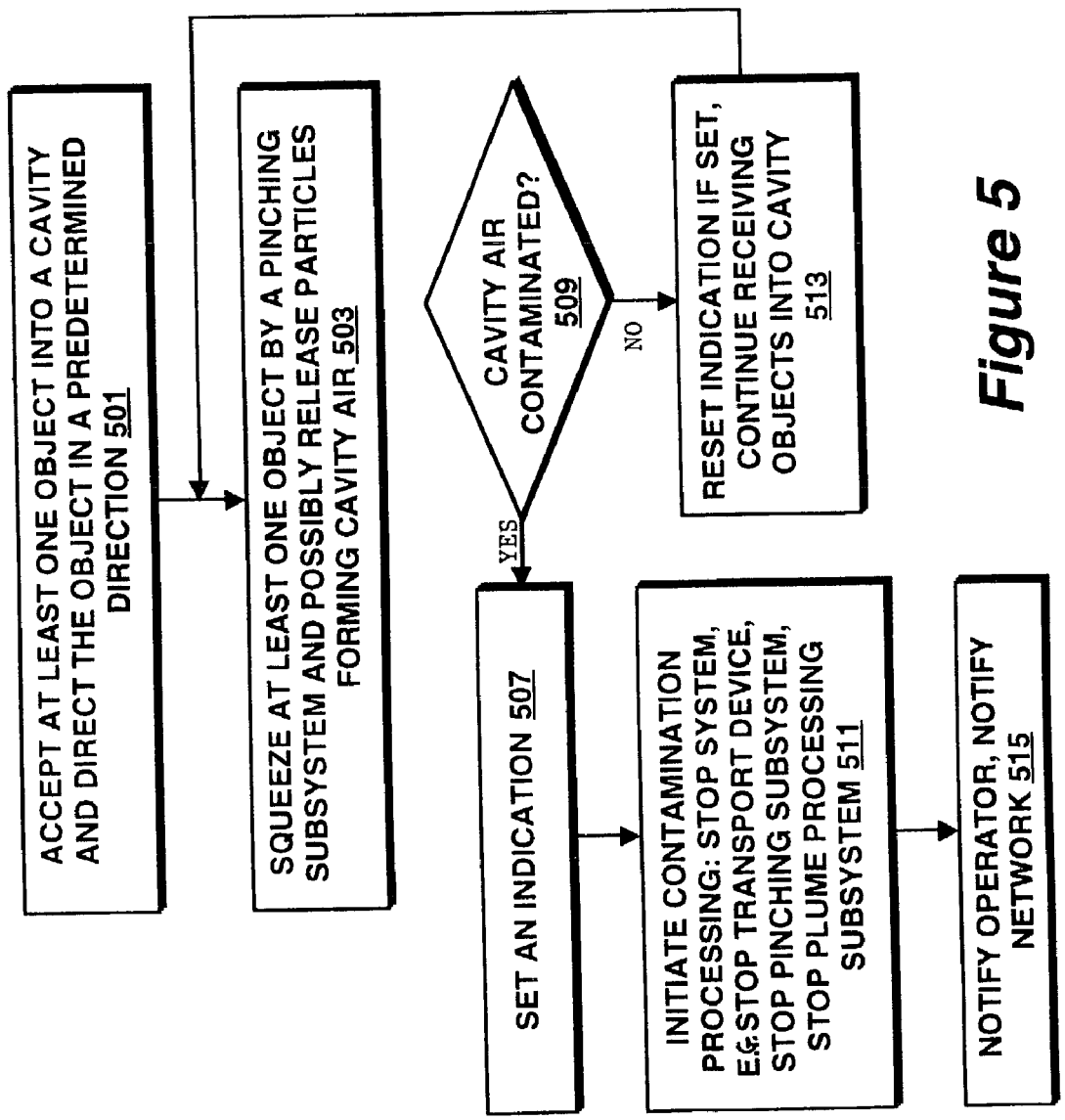
FIG. 5 is a flowchart of the method of the illustrative embodiment of the present invention.

Referring now to FIG. 5, the method of the illustrative embodiment of the present invention includes a first step of accepting at least one object into a cavity defined by a closed chamber having a sealable inlet to the cavity (method step 501). The step of accepting directs the object substantially onto a travel path in a direction of travel. The method next includes the step of pinching or squeezing at least one object by a pinching subsystem and releasing particles into air within the cavity forming cavity air (method step 503). By this step, the object is compressed and may release particles into the cavity. Optionally, the step of pinching can further include the steps moving at least one object between juxta-positioned rollers such as a rotating left roller and a rotating right roller, where the left roller is substantially adjacent to the right roller, the left roller is sufficiently spaced from the right roller to allow constricted passage of at least one object, and the left roller rotates clockwise while the right roller rotates counterclockwise. Other roller or pinching designs may be used. For example, the juxtapositional rollers may be one on top of the other, if the object to be pinched or squeezed comes in from the side.

Continuing to refer to FIG. 5, the method next includes the steps of testing the cavity air for contamination (decision step 509), and setting an indication if the cavity air is contaminated (method step 507). The method of the present invention can optionally include the step of drawing the cavity air through a tube into a pathogen detection subsystem. After the indication is set, the method of the present invention can optionally include the steps of initiating contamination processing that can include the steps of stopping the pinching subsystem and stopping the cavity air processing subsystem (method step 511) and notifying the operator and network of the contamination (method step 515). If no contamination is detected, the system can reset any indication that is set and continue receiving objects into the cavity through the sealable inlet (method step 513).

The method of the present invention can optionally include, preceding the step of accepting at least one object into the cavity, the step of depositing from a tub through an airtight connection at least one object into the cavity. The method can further optionally include the step of conveying at least one object from the sealable inlet to the pinching subsystem substantially in the travel path and substantially in the direction of travel by use of a transport device within the cavity. The method can further optionally include the step of preparing at least one object for entry into the pinching subsystem. This step of preparing, in the illustrative embodiment, takes the form of singulating the mail piece from neighboring pieces so that the singulated piece can properly exit the cavity through the pinching subsystem.

The method of the illustrative embodiment can further optionally include the steps of sequencing operations among the pinching subsystem, the transport device, and the cavity air processing subsystem, and transmitting the indication through a computer network.

Although the invention has been described with respect to various embodiments it should be realized this invention is also capable of a wide variety of further and other embodiments within the spirit and scope of the present invention.

What is claimed is:

1. A system for detecting contaminated objects comprising:
   a closed chamber defining a cavity, said chamber having a sealed inlet to accept at least one object into said cavity, said chamber being substantially airtight, said sealable inlet being sealed from the ambient atmosphere during acceptance of objects into said cavity;
   a compressing assembly for receiving the object and compressing the object to release particles associated with the object into air within said cavity;
   a cavity air processing assembly for receiving the air within said cavity and subjecting the air to at least one test; and
   an indicator assembly for providing an indication of results obtained from such test, wherein based upon such indication, a decision can be made with respect to further handling of the object; said sealable inlet including an accommodation for a tub defining an interior, said tub being compatibly shaped with respect to said sealable inlet and cooperating therewith to provide a seal which prevents ambient air from entering said tub or said cavity.

2. The system as in claim 1 further comprising:
   a transport device following a path and direction of normal travel within said cavity, said path extending substantially from said sealable inlet to said pinching subsystem; and
   a transport power supply driving said transport device.

3. The system as in claim 2 wherein said transport device further comprises a conveyor belt.

4. The system as in claim 1 wherein said sealable inlet is constructed and arranged to accept a plurality of objects into said cavity simultaneously.

5. The system as in claim 1 wherein said sealable inlet has an edge and said tub has a rim, said edge and rim being constructed and arranged to cooperatie together to provide a seal from ambient air.

6. The system as in claim 1 wherein said inlet is sealed from the ambient atmosphere while objects are placed into the chamber.

7. The system as in claim 1 wherein said sealable inlet further comprises: a sealable inlet edge; and a cover spanning said sealable inlet, wherein said cover interlocks with said sealable inlet edge forming a first airtight seal.

8. The system as in claim 1 further comprising:
   a controller capable of sequencing operations between said pinching subsystem and said cavity air processing subsystem.

9. The system as in claim 8 further comprising:
   a computer network connection, said computer network connection being capable of electronic communication with said controller.

10. The system as in claim 9 wherein said cavity air processing subsystem further comprises:
    a pathogen detection subsystem capable of testing said cavity air for contamination, said pathogen detection subsystem capable of setting an indication whenever said cavity air is contaminated; and
    a tube capable of providing fluid communication between said cavity and said pathogen detection subsystem, said pathogen detection subsystem transmitting a first signal to said controller whenever said cavity air is contaminated, said controller transmitting said indication through said computer network connection.

11. The system as in claim 1 further comprising:
    a controller capable of sequencing operations among said pinching subsystem, said cavity air processing subsystem, and said transport device.

12. The system as in claim 11 wherein said cavity air processing subsystem further comprises:
    a pathogen detection subsystem capable of testing said cavity air for contamination, said pathogen detection subsystem capable of setting an indication whenever said cavity air is contaminated; and
    a tube capable of providing fluid communication between said cavity and said pathogen detection subsystem, said pathogen detection subsystem transmitting a first signal to said controller whenever said cavity air is contaminated, said controller transmitting said indication through said computer network connection, said controller transmitting a second signal to said pinching subsystem power supply stopping said pinching subsystem and said controller transmitting a third signal to said transport power supply stopping said transport means.

13. The system as in claim 1 wherein said cavity air processing subsystem further comprises:
    a pathogen detection subsystem capable of testing said cavity air for contamination, said pathogen detection subsystem capable of setting an indication whenever said cavity air is contaminated; and a tube capable of providing fluid communication between said cavity and said pathogen detection subsystem.

14. The system of claim 1 wherein said sealable inlet is constructed and arranged to accept a plurality of objects into said cavity simultaneously.

15. A system for detecting contaminated objects comprising:
    a closed chamber defining a cavity, said chamber having a sealable inlet to accept at least one object into said cavity;
    a pinching subsystem operably connected to said cavity for receiving said object and compressing said object and releasing particles associated with said object into air within said cavity to form cavity air;
    a cavity air processing subsystem operably connected to said cavity for receiving said cavity air and subjecting said cavity air to at least one test; and
    a means for providing an indication of results obtained from said test, wherein based upon said indication, a decision can be made with respect to further handling of said object; and
    said sealable inlet including an accommodation for a tub defining an interior, said tub having a tub rim compatibly shaped with said sealable inlet edge, said tub having a lid covering said tub rim, wherein said tub rim interlocks with said sealable inlet edge forming a second airtight seal, and wherein said lid interlocks with said tub rim forming a third airtight seal.

16. A system for detecting contaminated objects comprising:
- a closed chamber defining a cavity, said chamber having a sealable inlet to accept at least one object into said cavity, said chamber being substantially airtight;
- a pinching subsystem operably connected to said cavity for receiving said object and compressing said object and releasing particles associated with said object into air within said cavity to form cavity air;
- a cavity air processing subsystem operably connected to said cavity for receiving said cavity air and subjecting said cavity air to at least one test;
- a means for providing an indication of results obtained from said test, wherein based upon said indication, a decision can be made with respect to further handling of said object
- a sealable inlet edge;.
- a cover spanning said sealable inlet, wherein said cover interlocks with said sealable inlet edge forming a first airtight seal; and
- a separator mechanism for preparing said object to enter said pinching subsystem, and wherein said separator mechanism is within said cavity and said pinching subsystem is connected to said cavity and delivers objects from said cavity .

17. A system for detecting contaminated objects comprising:
- a closed chamber defining a cavity, said chamber having a sealable inlet to accept at least one object into said cavity, said chamber being substantially airtight;
- a pinching subsystem operably connected to said cavity for receiving said object and compressing said object and releasing particles associated with said object into air within said cavity to form cavity air;
- a cavity air processing subsystem operably connected to said cavity for receiving said cavity air and subjecting said cavity air to at least one test;
- a means for providing an indication of results obtained from said test, wherein based upon said indication, a decision can be made with respect to further handling of said object;
- a conveyor for moving objects along a conveying path; and
- said sealable inlet including an accommodation for a tub defining an interior, said tub having a tub rim compatibly shaped with said sealable inlet edge, said tub having a lid covering said tub rim, wherein said tub rim interlocks with said sealable inlet edge forming a second airtight seal, and wherein said lid interlocks with said tub rim forming a third airtight seal.

18. The system as in claim 17 wherein said sealable inlet is sealed from the ambient atmosphere during the acceptance of objects into said cavity.

\* \* \* \* \*

UNITED STATES PATENT AND TRADEMARK OFFICE
CERTIFICATE OF CORRECTION

| | | |
|---|---|---|
| PATENT NO. | : 7,194,924 B2 | Page 1 of 1 |
| APPLICATION NO. | : 10/208960 | |
| DATED | : March 27, 2007 | |
| INVENTOR(S) | : Michael A. Wisniewski et al. | |

It is certified that error appears in the above-identified patent and that said Letters Patent is hereby corrected as shown below:

On the cover page, under (56) References Cited, and further under U.S. PATENT DOCUMENTS, please add the following:

-- 5,760,585    7/1998  Clark et al. ...................250/455.11 --

Signed and Sealed this

Twenty-second Day of May, 2007

JON W. DUDAS
*Director of the United States Patent and Trademark Office*